(12) United States Patent
Lock et al.

(10) Patent No.: US 10,318,863 B2
(45) Date of Patent: Jun. 11, 2019

(54) SYSTEMS AND METHODS FOR AUTOCONFIGURATION OF PATTERN-RECOGNITION CONTROLLED MYOELECTRIC PROSTHESES

(71) Applicant: Rehabilitation Institute of Chicago, Chicago, IL (US)

(72) Inventors: Blair Lock, Chicago, IL (US); Levi Hargrove, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 707 days.

(21) Appl. No.: 13/950,000

(22) Filed: Jul. 24, 2013

(65) Prior Publication Data

US 2014/0032462 A1    Jan. 30, 2014

Related U.S. Application Data

(60) Provisional application No. 61/675,147, filed on Jul. 24, 2012.

(51) Int. Cl.
| | |
|---|---|
| *G16H 50/00* | (2018.01) |
| *A61B 5/0488* | (2006.01) |
| *A61F 2/72* | (2006.01) |
| *A61B 5/00* | (2006.01) |
| *A61F 2/54* | (2006.01) |
| *G06N 3/08* | (2006.01) |
| *G05B 13/02* | (2006.01) |
| *A61F 2/50* | (2006.01) |
| *A61F 2/70* | (2006.01) |

(Continued)

(52) U.S. Cl.
CPC ........... *G06N 3/08* (2013.01); *A61B 5/04888* (2013.01); *A61B 5/7267* (2013.01); *A61F 2/54* (2013.01); *A61F 2/72* (2013.01); *G05B 13/0265* (2013.01); *A61F 2002/5036* (2013.01); *A61F 2002/704* (2013.01); *A61F 2002/7615* (2013.01); *G16H 50/00* (2018.01)

(58) Field of Classification Search
None
See application file for complete search history.

(56) References Cited

U.S. PATENT DOCUMENTS

| | | |
|---|---|---|
| 4,209,860 A | 7/1980 | Graupe |
| 4,314,379 A | 2/1982 | Tanie et al. |

(Continued)

FOREIGN PATENT DOCUMENTS

| | | | | |
|---|---|---|---|---|
| EP | 1 043 003 A1 | * 10/2000 | ................ | A61F 2/72 |
| WO | WO 01/13778 A2 | * 3/2001 | ................ | A61F 2/72 |

*Primary Examiner* — David H Willse
(74) *Attorney, Agent, or Firm* — Polsinelli PC; Ari M. Bai

(57) ABSTRACT

Embodiments of the invention provide for a prosthesis guided training system that includes a plurality of sensors for detecting electromyographic activity. A computing device, which can include a processor and memory, can extract data from the electromyographic activity. A real-time pattern recognition control algorithm and an autoconfiguring pattern recognition training algorithm can be stored in the memory. The computing device can determine movement of a prosthesis based on the execution of the real-time pattern recognition control algorithm. The computing device can also alter operational parameters of the real-time pattern recognition control algorithm based on execution of the autoconfiguring pattern recognition training algorithm.

19 Claims, 6 Drawing Sheets

(51) Int. Cl.
*A61F 2/76* (2006.01)
*A61F 2/56* (2006.01)

(56) References Cited

U.S. PATENT DOCUMENTS

| | | |
|---|---|---|
| 5,888,213 A | 3/1999 | Sears et al. |
| 6,272,479 B1 | 8/2001 | Farry et al. |
| 6,679,920 B2 | 1/2004 | Biedermann et al. |
| 6,785,574 B2 | 8/2004 | Kajitani et al. |
| 6,859,663 B2 | 2/2005 | Kajitani et al. |
| 7,260,436 B2 | 8/2007 | Kilgore et al. |
| 7,881,780 B2 | 2/2011 | Flaherty |
| 7,991,461 B2 | 8/2011 | Flaherty et al. |
| 8,060,194 B2 | 11/2011 | Flaherty |
| 8,437,844 B2 | 5/2013 | Momen et al. |
| 8,828,093 B1* | 9/2014 | Kuiken .................... A61F 2/60 623/25 |
| 2003/0050569 A1 | 3/2003 | Shenoy et al. |
| 2003/0139783 A1 | 7/2003 | Kilgore et al. |
| 2005/0182341 A1 | 8/2005 | Katamaya et al. |
| 2006/0167371 A1 | 7/2006 | Flaherty et al. |
| 2011/0060461 A1* | 3/2011 | Velliste .............. A61B 5/04888 700/254 |
| 2012/0101596 A1 | 4/2012 | Dietl |
| 2014/0277583 A1* | 9/2014 | Kuntaegowdanahalli ................... A61F 2/72 623/25 |

* cited by examiner

| Questionnaire Likert-Item | Avg (Std) |
|---|---|
| I would be able to use a pattern recognition-controlled prosthesis at home if I could train it myself. | 5 (0) |
| I would be able to notice when it is necessary to re-train ("refresh") my prosthesis. | 4.8 (0.4) |
| Prosthesis guided training system is intuitive; the directions are clear and easy to follow. | 5 (0) |
| Prosthesis guided training system is tiring. | 1.8 (1.2) |
| Having the motions presented to me in a consistent order helps me complete Prosthesis guided training system. | 5 (0) |
| I would feel comfortable training my prosthesis using Prosthesis guided training system in front of people I did not know. | 4.6 (0.8) |

FIGURE 6

| Questionnaire Fill-In-The-Blank Question | Avg (Std) |
|---|---|
| I would be willing to spend up to _____ minutes to train my prosthesis each time I put it on. | 5.5 (4.9) |
| If it were possible, I would be willing to "refresh" the control of my prosthesis while I am wearing it up to _____ times per day. | 3.2 (1.7) |
| If it were possible, I would be willing to "refresh" the control of my prosthesis while I am wearing it no more than about every _____ hours. | 2.4 (1.6) |
| From my experiences with it thus far, I would be willing to use the prosthesis guided training system _____ times in a row in an attempt to get good control back instead of taking the prosthesis off. | 3.2 (1.5) |

FIGURE 7

SYSTEMS AND METHODS FOR AUTOCONFIGURATION OF PATTERN-RECOGNITION CONTROLLED MYOELECTRIC PROSTHESES

CROSS REFERENCE TO RELATED APPLICATIONS

This application is a non-provisional that claims benefit to U.S. Provisional Patent Application No. 61/675,147, filed on Jul. 24, 2012, which is herein incorporated by reference in its entirety

STATEMENT REGARDING FEDERALLY SPONSORED RESEARCH OR DEVELOPMENT (IF APPLICABLE)

This invention was made with Government support under Grant No. R-01-HD-05-8000 awarded by the Department of Health and Human Services, National Institutes of Health. The Government has certain rights in the invention.

FIELD

This disclosure relates generally to the field of human-machine interfaces, and in particular to a system and method for autoconfiguring pattern-recognition controlled myoelectric prostheses.

BACKGROUND

Myoelectric prostheses, which rely on electromyography (EMG) signals to control joint movement, are often used to effectively treat upper-limb amputation. The control principles used in commercially available prostheses have been available for many decades and rely on an estimate of the amplitude of strategically placed electrodes coupled with simple rules to form control signals for controlling the operation of the prosthesis. Only a limited number of movements may be restored and to achieve a particular task for movement of the prosthesis, and the movements must be controlled sequentially as only one motion may be controlled at a time.

Pattern recognition has also been used to extract control signals for prosthetic limbs. However, in order to achieve optimal or near-optimal use of the pattern-recognition controlled prosthetic limb, example data related to each type of limb movement should be recorded from each patient to train, configure, and calibrate prosthesis movement. In addition to configuring or training the prosthesis prior to initial use, prosthesis users may be required to reconfigure the prosthesis to maintain performance levels. Conventional pattern recognition training systems often require additional hardware and technological capacity, which can hamper the user's capability to reconfigure the prosthesis.

SUMMARY

In some embodiments a prosthesis guided training system can include a plurality of sensors for detecting electromyographic activity. A computing device, which can include a processor and memory, extracts data from the electromyographic activity. A real-time pattern recognition control algorithm and an autoconfiguring pattern recognition training algorithm are at least partially stored in the memory. In one embodiment, the computing device determines movement of a prosthesis based on the execution of the real-time pattern recognition control algorithm by the processor. The computing device can also alter operational parameters of the real-time pattern recognition control algorithm based on the processor executing the autoconfiguring pattern recognition training algorithm.

Additional objectives, advantages and novel features will be set forth in the description which follows or will become apparent to those skilled in the art upon examination of the drawings and detailed description which follows.

BRIEF DESCRIPTION OF THE DRAWINGS

FIGS. 6 and 7 are tables that depict averaged test subject responses to questionnaire items.

Corresponding reference characters indicate corresponding elements among the view of the drawings. The headings used in the figures do not limit the scope of the claims.

DETAILED DESCRIPTION

Figure 1:
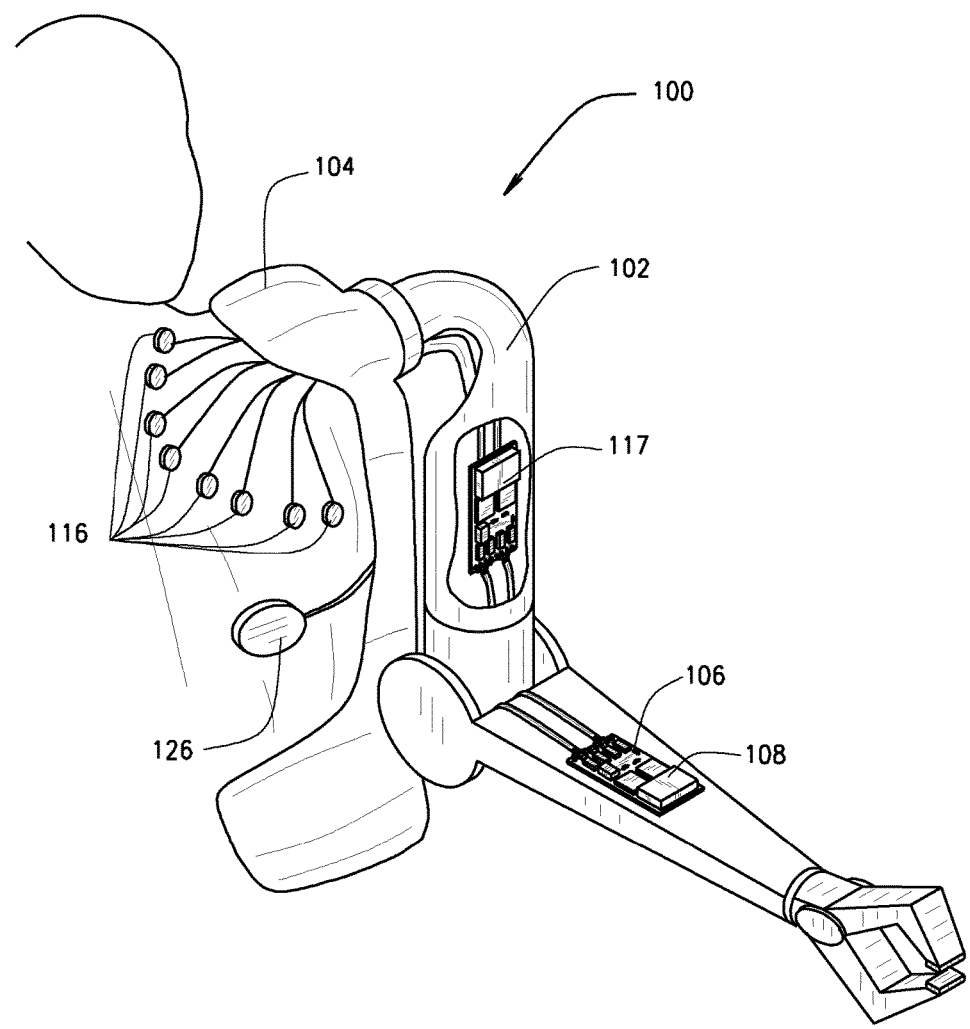
FIG. 1 is a simplified illustration of one embodiment of a prosthesis guided training system.

Referring to the drawings, embodiments of a prosthesis guided training system are illustrated and generally indicated as 100 in FIG. 1. In one embodiment, the prosthesis guided training system 100 can include a prosthesis 102 that is fitted to an individual 104. More specifically, the prosthesis 102 can be configured to operate as a myoelectrically-controlled device that can be professionally custom fit for the user 104. For example, as shown in FIG. 1, in one embodiment, the prosthesis 102 can be configured as a prosthetic limb for an individual with a shoulder disarticulation. In other embodiments, the prosthesis 102 can be configured differently, such as a prosthetic limb for individuals 104 with transradial and/or transhumoral amputations. In yet other embodiments, the prosthesis 102 can be configured for individuals 104 with amputations or disarticulations of other limbs.

Figure 2:
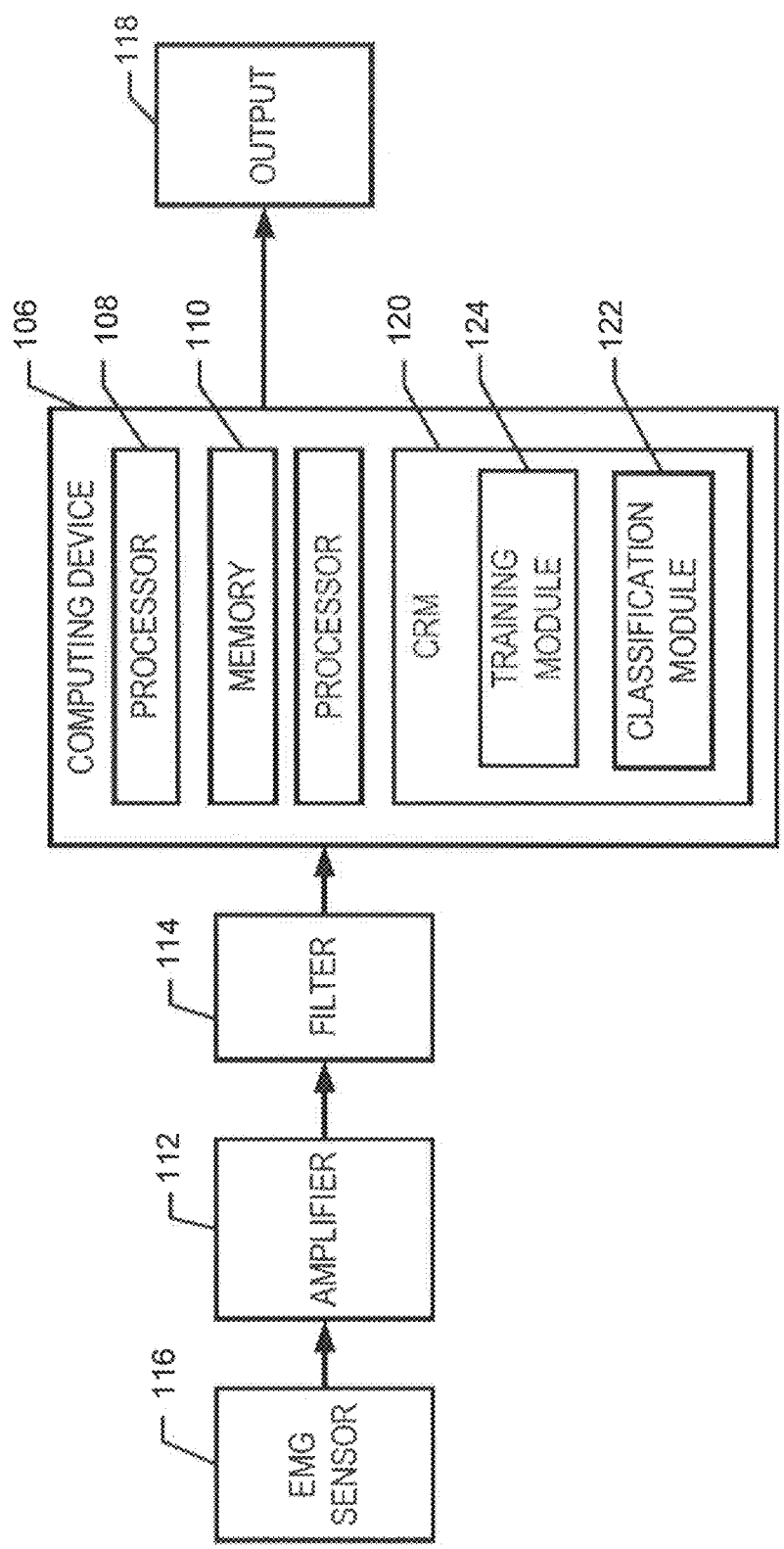
FIG. 2 is a simplified block diagram of one embodiment of a computing device and related components for the prosthesis guided training system.

Referring to FIGS. 1 and 2, in one embodiment the prosthesis guided training system 100 includes a computing device 106 for controlling the operation of one or more prosthesis 102. In some embodiments, the computing device 106 may include at least one processor 108 in operative communication with a memory 110. For example, the computing device 106 may be a personal computer, workstation, server, or mobile device, while the processor 108 may be a hardware device that processes software, other machine-readable instructions, retrieved data, and/or received data. In addition, the memory 110 may store software or other machine-readable instructions and data. The memory 110 may also include volatile and/or non-volatile memory. The memory 110 may include a database to store data related to parameters for various components of the prosthesis guided training system 100, one or more prostheses 102, one or more electromyography (EMG) signal patterns, or any other data. The computing device 106 may further include various hardware and accompanying software components, such as a signal amplifier 112 or a signal filter 114, that may be configured for receiving EMG signal data from one or more EMG sensors 116, via a signal input device 117, and generating an output 118 that may be used in prosthesis 102 operations. For example, EMG signals can be collected by the EMG sensors 116, transmitted to the signal input device 117 such that the EMG signal data can be conditioned and later transmitted to the computing device 106 for additional processing.

In addition, the computing device 106 may also include a communication system to communicate with one or more components of the prosthesis guided training system 100, such as the EMG sensors 116, and/or other sensors and/or computing devices and systems, over a communication network via wireline and/or wireless communications, such as through the Internet, an intranet, and Ethernet network, a wireline network, a wireless network. The computing device 106 may further include a display (not shown) for viewing data or one or more user interfaces (UI), such as a computer monitor, and an input device (not shown), such as a keyboard or a pointing device (e.g., a mouse, trackball, pen, touch pad, or other device) for entering data and navigating through data, including images, documents, structured data, unstructured data, HTML pages, other web pages, and other data.

The computing device 106 may include a database (not shown) and/or is configured to access the database. The database may be a general repository of data including, but not limited to user data, patient data, historical training data, or algorithms, among others. The database may include memory and one or more processors or processing systems to receive, process, query and transmit communications and store and retrieve such data. In another aspect, the database may be a database server.

According to one aspect, the computing device 106 includes a computer readable medium ("CRM") 120, which may include computer storage media, communication media, and/or any another available media that can be accessed by the processor 108. For example, CRM 120 may include non-transient computer storage media and communication media. By way of example and not limitation, computer storage media includes memory, volatile media, nonvolatile media, removable media, and/or non-removable media implemented in a method or technology for storage of information, such as machine/computer readable/executable instructions, data structures, program modules, or other data. Communication media includes machine/computer readable/executable instructions, data structures, program modules, or other data and includes an information delivery media or system. Generally, program modules include routines, programs, instructions, objects, components, data structures, etc., that perform particular tasks or implement particular abstract data types.

By way of example and not limitation, the CRM 120 may store executable instructions to execute a real-time pattern recognition control algorithm 200 (FIG. 3) at a classification module 122 or an autoconfiguring pattern recognition training algorithm 300 (FIG. 4) at a training module 124. More specifically, in one embodiment, during an initial setup and configuration of the prosthesis guided training system 100 the computing device 106 can cause the processor 108 to execute the autoconfiguring pattern recognition training algorithm 300, as described in further detail below. Moreover, during conventional operations of the prosthesis 102 (i.e., day-to-day, real-time activities), the computing device 106 can cause the processor 108 to execute the real-time pattern recognition control algorithm 200, as described in further detail below.

Referring back to FIG. 1, in some embodiments, the computing device 106 can be incorporated with the prosthesis 102. As a result, the processor 108 can execute or perform the real-time pattern recognition control algorithm 200 and/or the autoconfiguring pattern recognition training algorithm 300 and the output 120 need not be relayed to a remote prosthesis 102 because of the integral nature of the computing device 106 and the prosthesis 102. Alternately, the computing device 106 can be remotely positioned with respect to the prosthesis 102 so that the output 120 is transmitted to the prosthesis 102 from a remote location.

Figure 3:
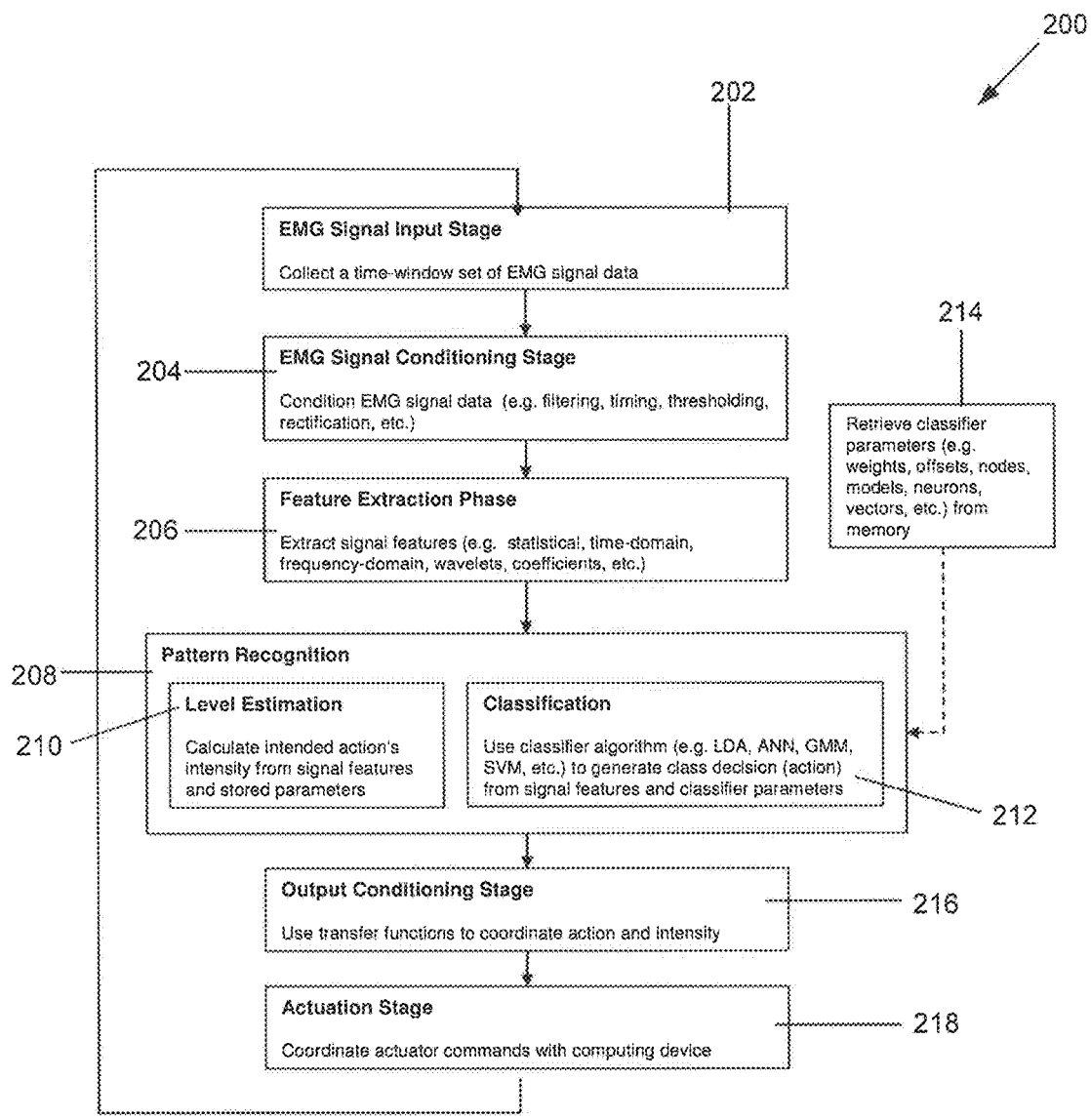
FIG. 3 is a flow chart illustrating the operation of a real-time pattern recognition control algorithm for the prosthesis guided training system.

FIG. 3 illustrates one method for executing the real-time pattern recognition control algorithm 200. In some embodiments, the processor 108 of the computing device 106 executes the real-time pattern recognition control algorithm 200. In one embodiment, the processor 108 can initiate the real-time pattern recognition control algorithm 200 at an EMG signal data input stage 202, wherein an EMG signal data is acquired from the signal input device 117 based on a predetermined time interval. For example, the predetermined time interval can extend for a relatively short time period, such as between 100-250 milliseconds (ms).

After collection, the EMG signal data is transmitted to an EMG signal data conditioning stage 204. At the EMG signal data conditioning stage 204, operations such as, but not limited to, signal filtering, time aligning, thresholding, rectification, and other suitable signal conditioning processes are executed. The processor 108 executes a feature extraction phase 206, such that the EMG signal data obtained during a particular predetermined time interval is further processed, reduced, and/or extracted. By way of example only, portions of the EMG signal data can be extracted based on the presence of one or more signal features, which can include, but are not limited to time-based signal features such as zero-crossings, slope sign changes, waveform length, root-mean-square, and/or mean-absolute value; frequency-based signal features such as wavelet transforms, wavelet packets, and/or Fourier transforms; and other autoregressive model coefficients.

After the feature extraction phase 206, the processed and extracted EMG signal data may be transmitted to a pattern recognition stage 208, such that the processor 108 may compute level estimation 210 and classification 212. In one embodiment, a classification operation 212 executes an algorithm, such as linear discriminant analysis (LDA), which may be used to identify an output class of user intent from the input set of EMG signal data (i.e., the direction and type of movement that the individual 104 wishes the prosthesis 102 to move). In some embodiments, classification operation 212 can execute other algorithms in addition to, or in lieu of LDA, including a Gaussian mixture model (GMM), a support vector machine (SVM), or an artificial neural network (ANN). When identifying the output class from the input set of EMG signal data, classification operation 212 employs a set of parameters such as: boundary-defining weights and offsets; neural network node information; and/or comparative models.

In one embodiment, a level estimation stage 210 can be used by the computing device 106 to compare an intensity of the processed EMG signal data to a set of stored signal parameters 214, as shown in FIG. 3. As a result of level estimation stage 210, the computing device 106 can determine a scaling factor of the output class' intensity level (i.e., a magnitude of force or level of actuation with which the prosthesis 102 will move). The stored signal parameters 214 can include dynamic ranges of sets of calibration signals, such as weights, offsets, nodes, models, neurons, vectors, and other suitable data that can be stored in the memory 110 (FIG. 2). Some or all of the stored signal parameters 214 can be created or modified during execution of the autoconfiguring pattern recognition training algorithm 300.

As further shown in FIGS. 1 and 3, after the pattern recognition stage 208, the processed EMG signal data can be further processed at an output conditioning stage 216. The output conditioning stage 216 can combine the output class of motion intent (i.e., the result of classification 212) and estimated level of actuation (i.e., the result of level estimation 210) and use a transfer functionality to coordinate the processes of the prosthesis 102 such as rate-limiters, ramp activations, and exponential output profiles. Finally, at an actuation stage 218, the processor 108 converts the data resulting from the output conditioning stage 216 to commands appropriate for the computing device 106 to direct the movement of the prosthesis 102. In some embodiments, the real-time pattern recognition control algorithm 200 can be continuously repeated when the prosthesis guided training system 100 is in a real-time operation mode (e.g., in a non-training mode for day-to-day operations).

Figure 4:
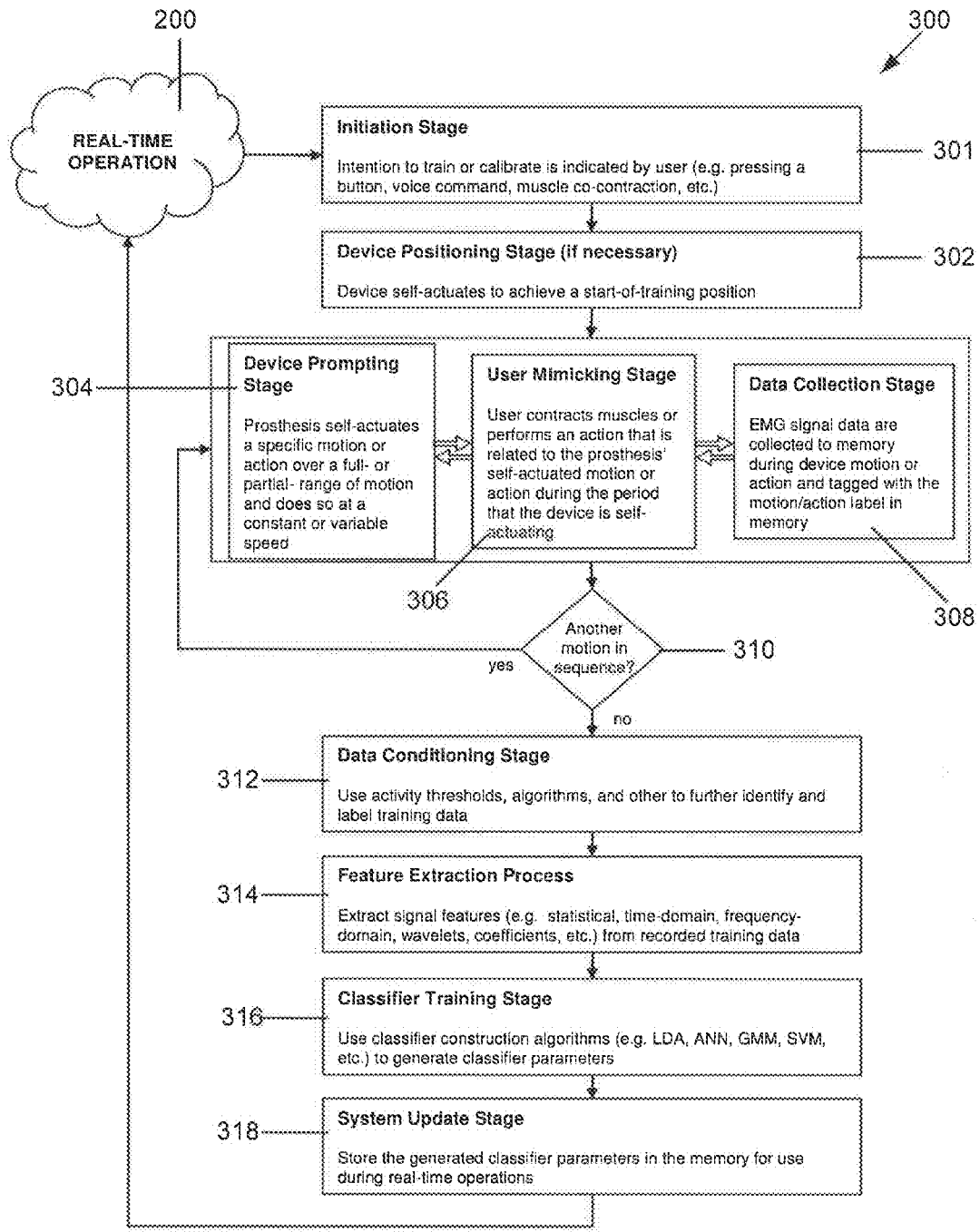
FIG. 4 is a flow chart illustrating the operation of an autoconfiguring pattern recognition training algorithm for the prosthesis guided training system.

Referring now to FIG. 1, in one embodiment, the prosthesis guided training system 100 can include a training activation button 126 that is in communication (e.g., wired or wireless communication) with the computing device 106. More specifically, the individual 104 can actuate, depress, and/or otherwise contact the training activation button 126 to initiate the processor 108 to execute the autoconfiguring pattern recognition training algorithm 300 (FIG. 4). For example, the individual 104 can press the training activation button 126 for a predetermined time (e.g., about two seconds) to start the autoconfiguring pattern recognition training algorithm 300. By requiring that the individual 104 depress the training activation button 126 for a predetermined time, accidental activation of the autoconfiguring pattern recognition training algorithm 300 can be avoided. In other embodiments, in addition to, or in lieu of the training activation button 126, the prosthesis guided training system 100 can be configured so that the individual 104 may execute the autoconfiguring pattern recognition training algorithm 300 via voice command, a body-powered analog input switch, a muscle co-contraction, a specific output class of motion, and/or any other suitable manner of activation.

FIG. 4 illustrates one method for executing the autoconfiguring pattern recognition training algorithm 300. In some embodiments, the autoconfiguring pattern recognition training algorithm 300 can be executed at any time. More specifically, the autoconfiguring pattern recognition training algorithm 300 can be executed before, during, and after the real-time pattern recognition control algorithm 200 is executed. For example, during use of the prosthesis 102, the individual 104 can assess the responsiveness, accuracy, and/or dexterity of the prosthesis 102. If the individual 104 wishes to retrain or recalibrate the prosthesis 102, the individual 104 can execute the autoconfiguring pattern recognition training algorithm 300 at an initiation stage 301. For example, the initiation stage 301 can include the individual 104 pressing the training activation button 126 to execute the autoconfiguring pattern recognition training algorithm 300.

Once executed, the autoconfiguring pattern recognition training algorithm 300 assesses a position of the prosthesis 102. More specifically, as noted above, the autoconfiguring pattern recognition training algorithm 300 can be executed during operations of the real-time pattern recognition control algorithm 200 (FIG. 3). As a result, the prosthesis 102 may be in use (e.g., wrist flexed, elbow in an extended position, hand in an closed position, etc.) so that the prosthesis 102 may have to be returned to a resting position prior to continuing execution of the autoconfiguring pattern recognition training algorithm 300. By way of example only, the computing device 106 may need to perform an optional step at a device positioning stage 302. At the device positioning stage 302, if the prosthesis 102 is in a non-resting position, the autoconfiguring pattern recognition training algorithm 300 may require that the prosthesis 102 return to a resting position (i.e., a home position) by coordinating self-actuation commands. At device positioning stage 302, the individual 104 ensures that the prosthetic device 102 is in a known starting position and orientation (i.e., for the purposes of calibration and realignment). At device positioning stage 302 may include inherent motor and joint position data as well as timed endpoint homing sequences.

In one embodiment, after the prosthesis 102 is in the required position, the processor 108 executes a device prompting stage 304, wherein the prosthesis 102 self-actuates or moves in one or more different directions, motions, or sequences of directions and motions. The self-actuations or movements can be used to direct the individual 104 to contract his or her muscles to mimic performing the self-actuation of the prosthesis 102. Moreover, the self-actuations can occur at a variable or a constant speed. During the device prompting stage 304, the computing device 106 can execute a user mimicking stage 306 to cause the individual 104 to generate EMG signal data corresponding to the self-actuation or movements of the prosthesis 102. At the same time or substantially the same time, a data collection operation 308 can also be executed so that the individual-specific 104 EMG signal data can be collected and stored in the memory 110 with an appropriate indicator denoting the type of movement associated with the particular EMG signal data set.

For example, at device prompting stage 304, the individual mimicking stage 306, and data collection operation 308, the prosthesis 102 moves so that a joint of the prosthesis 102 (e.g., the wrist) flexes, extends, or articulates in any other suitable orientation in a predetermined sequence. While visualizing the prosthesis 102 movements, the individual 104 can generate muscle contractions or may attempt to mimic the activity being performed by the prosthesis 102 and the EMG signal data generated by the individual 104 is captured and stored in the memory 110. In other words, during or after the prosthesis 102 prompts the individual 104 with a movement, the individual 104 can mimic that movement with muscle contractions and the EMG signal data received by the EMG signal sensors 116 can be stored in the memory 110 with an appropriate indicator of the movement type. Additionally, after movement of the prosthesis 102 is terminated, the individual 104 may also cease moving. After the user 104 stops mimicking the prosthesis' 102 movement and the prosthesis 102 returns to an at-rest or home position, the computing device 106 can store the EMG signal data from this relaxed or "no-motion" state as a basal or threshold level of EMG signal activity.

In one embodiment, the types of movements and the sequence of movements employed by the prosthesis 102 at device prompting stage 304 can be the same or substantially the same during each execution of the autoconfiguring pattern recognition training algorithm 300. As a result, the quality and repeatability of the elicited EMG signal data can be improved, as can the individual's 104 comfort level with the prosthesis guided training system 100. Also, by repeating the sequence and movements, a number of sessions required to produce satisfactory performance of the prosthesis guided training system 100 can be reduced.

As further shown in FIG. 4, after the computing device 106 stores the EMG signal data for a particular self-actuation of the prosthesis 102, the autoconfiguring pattern recognition training algorithm 300 reaches a decision point 310. At the decision point 310, the computing device 106 determines whether any additional EMG signal data related to other movements is still required to complete execution of the autoconfiguring pattern recognition training algorithm 300. For example, in embodiments where the prosthesis 102 is for an individual 104 with a transhumeral amputation, execution of the autoconfiguring pattern recognition training algorithm 300 may require EMG signal data from elbow motions, wrist motions, and hand motions to complete the calibration process. Accordingly, at the decision point 310, the computing device 106 determines whether sufficient EMG signal data related the possible prosthesis 102 motions has been gathered and stored in the memory 110. If sufficient EMG signal data has been gathered and stored (i.e., "yes" in FIG. 4), the autoconfiguring pattern recognition training algorithm 300 may proceed to the next steps. If the computing device 106 determines that there is insufficient EMG signal data stored in the memory 110 (i.e., "no" in FIG. 4), the device prompting stage 304, the individual mimicking stage 306, and data collection operation 306 can be repeated until sufficient EMG signal data is stored in the memory 110.

In one embodiment, if the computing device 106 determines that sufficient EMG signal data has been stored in the memory 110, the autoconfiguring pattern recognition training algorithm 300 proceeds to process the stored data and complete the calibration of the prosthesis 102. The stored EMG signal data may be first processed at data conditioning stage 312. In the data conditioning stage 312, the computing device 106 employs activity thresholds, algorithms, and other methods to further identify, mark, and associate training data. After conditioning the EMG signal data, a feature extraction process 314 may be executed. Similar to the real-time pattern recognition control algorithm 200, the feature extraction process 314 further processes the EMG signal data. By way of example only, during operation of the feature extraction process 314, portions of the EMG signal data can be extracted based on the presence of one or more signal features, which can include, but are not limited to: time-based signal features such as zero-crossings, slope sign changes, waveform length, root-mean-square, and/or mean-absolute value; frequency-based signal features such as wavelet transforms, wavelet packets, and/or Fourier transforms; and other auto-regressive model coefficients. In one embodiment, the feature extraction process 314 can differ from the feature extraction phase 206 in that the EMG signal data processed in the feature extraction phase 206 is time limited by the predetermined time interval. In other embodiments, the feature extraction process 314 and the feature extraction phase 206 can be the same or substantially the same process.

In one embodiment, after the feature extraction process 314, the processed EMG signal data may be passed to a classifier training stage 316. In the classifier training stage 316, the processed EMG signal data can be further processed using one or more algorithms (e.g., LDA, GMM, SVM, ANN, etc.) to define the stored signal parameters 214 to be used at the classification stage 212 of the real-time pattern recognition control algorithm 200. In one embodiment, the stored signal parameters 214 are stored in the memory 110 of the computing device 106 at system update stage 318, for application by the real-time pattern recognition control algorithm 200. After completion of the system update stage 318, the user 104 can enter or re-enter the real-time pattern recognition control algorithm 200 to continue non-training operations of the prosthesis 102.

In one embodiment, the autoconfiguring pattern recognition training algorithm 300 can include at least one additional step or stage that can be used to further establish basal or threshold EMG signal data. More specifically, after the device position stage 302, but before the device prompting stage 304, the prosthesis 102 can remain stationary for a short period of time before the computing device 106 begins the device prompting stage 304. During this stationary period, EMG signal data can be collected while the individual 104 remains in a substantially relaxed state. The EMG signal data gathered during this relaxed state can function as basal myoelectric activity and can be used to calculate a threshold for the EMG signal data generated during subsequent training, calibration, and configuring movements. Moreover, this additional stage can provide the computing device 106 with a comparison level of EMG activity when the user 104 neglects to mimic the self-actuating prosthesis 102 at device prompting stage 304. The threshold EMG signal data may provide additional training data for a "no-motion" category.

Additionally, some conventional training or calibration techniques may provide the individual 104 with an advanced warning prior to data collection stage 308. For example, conventional prosthesis-training techniques, such as screen-guided training, can provide a countdown (e.g., visual and/or auditory) prior to beginning data collection stage 308. As a result, the individual 104 can be prepared for data collection stage 308 and the computing device 106 does not necessarily detect significant background data. Because the prosthesis guided training system 100 does not rely on a training screen or auditory output, no advanced warning is provided to the individual 104. As a result, at least a portion of the EMG signal data collected during execution of the autoconfiguring pattern recognition training algorithm 300 can include background signals that do not reflect the individual 104 mimicking movement of the prosthesis 102. By creating an EMG signal data threshold, the stages of the autoconfiguring pattern recognition training algorithm 300 after data collection stage 308 can remove the non-useful portions of the EMG signal data, such as the delay that occurs before the individual 104 begins the user mimicking stage 306, but after initiation of the device prompting stage 304.

Figure 5A:
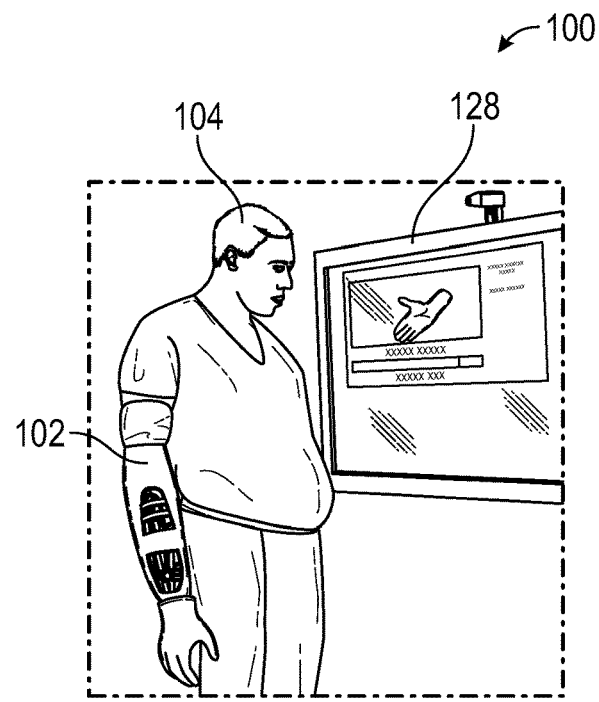
FIG. 5A is an image of a user employing a conventional prosthesis training system.
Figure 5B:
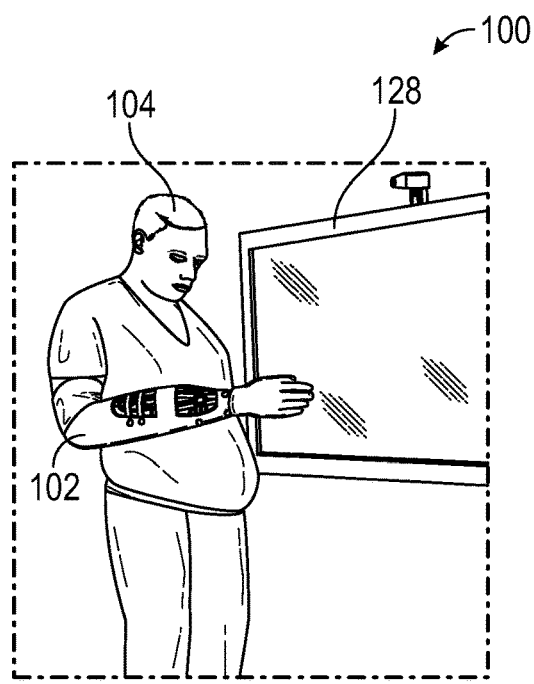
FIG. 5B is an image of a user employing one embodiment of a prosthesis guided training system.

By way of example only, FIGS. 5A and 5B depict a comparison of the prosthesis guided training system 100 and a conventional prosthesis training system. For example, the conventional prosthesis training system can be configured as a screen-guided training system, as shown in FIG. 5A. The conventional screen-guided training system can include prompting the individual 104 with visual and surrogate cues (i.e., virtual prosthesis 102 movements) displayed on a screen 128. As a result, the attention of the individual 104 is directed at the screen 128 while the device remains static and stationary. In comparison, in one embodiment, the prosthesis guided training system 100 does not employ the screen 128 so that the attention of the individual 104 can be focused on the dynamic motions and self-actions of the prosthesis 102 during the device prompting stage 304, the user mimicking stage 306, and data collection stage 308.

Relative to conventional, screen-guided training discussed above, the prosthesis guided training system 100 offers several advantages. First, the individual 104 can continue to wear the prosthesis 102 after decreased performance. Individuals 104 of some conventional screen-guided training systems are required to remove their prosthesis 102 should performance decline or the prosthesis 102 become unusable. For example, poor performance can originate from multiple causes, including broken or damaged parts, limb sweating, muscle fatigue, socket shift, and limb volume changes. Sometimes re-donning the prosthesis 102 can correct the problem; however, poor performance may require a visit to a prosthetist. No matter the issue, the prosthesis 102 may need to be removed or turned off, and this can occur at a time or place that can be inconvenient to the individual 104. Because of this inconvenience, some individuals 104 may choose to leave a prosthesis 102 at home. In comparison, with the prosthesis guided training system 100, at least some of the aforementioned issues that arise with the screen-guided training system can be overcome without having to disengage the prosthesis 102 or even needing to know what caused the decreased performance.

Second, the prosthesis guided training system 100 can eliminate some or all of the need for additional hardware or a surrogate-controlled prosthesis 102. As previously mentioned, the prosthesis guided training system 100 does not require a screen 128, monitor, or other visual display device. Accordingly, when the individual 104 needs to execute the autoconfiguring pattern recognition training algorithm 300, the individual 104 does not need to seek out a visual display with the specific screen-guided training software. As result, expenses can be reduced because of the reduced need for equipment. Moreover, requirements on product developers can be reduced because graphical user interface development and software maintenance costs are greatly reduced, as is the demand for high-quality, high-bandwidth device-to-computer communication.

Additionally, individuals 104 can quickly operate the prosthesis guided training system 100. More specifically, when the individual 104 dons the prosthesis 102 after a period of non-use, the individual 104 can quickly judge if they have acceptable control using what data is stored in the memory 110. If the individual 104 is unsatisfied, their prosthesis 102 may have been donned in a slightly differently manner, thereby causing EMG sensor 116 to shift, the individual 104 may be more rested or fatigued, may be performing contractions differently, or their skin conditions may have changed and that these changes may affect the execution of the real-time pattern recognition control algorithm 200. In these cases, the prosthesis guided training system 100 can help the individual 104 recalibrate their control of the prosthesis 102 and resume their activities of daily living. The execution of the autoconfiguring pattern recognition training algorithm 300 can be completed in about one minute. As a result, individuals 104 can relatively quickly complete the execution of the autoconfiguring pattern recognition training algorithm 300 in just about any location because there is no need for a screen 128 to complete the training process.

In some conventional training systems, the individual 104 or prosthetist may need to carefully adjust EMG signal gains, thresholds, boosts, and timings using a computer and proprietary graphical user interface. Moreover, many of these conventional systems do not rely on pattern recognition algorithms for day-to-day use of the prosthesis 102. Conversely, because the prosthesis guided training system 100 collects the EMG signal data for training, the collected and processed gains, thresholds, and boosts can be automatically set. The collected EMG signal data can be used to recalibrate an individual's 104 dynamic signal output range for each motion every time the autoconfiguring pattern recognition training algorithm 300 is executed. Furthermore, when the sequence of self-actuations or movements during the device prompting stage 304 incorporates a range of movement speeds, a larger dynamic range of EMG signal data intensities could be acquired as training data, thereby enhancing the robustness of the prosthesis guided training system 100.

Further, compared to conventional screen guided training systems, the prosthesis guided training system 100 offers a more real-time-like training and calibration experience, which can improve performance. When using a conventional screen guided training system, the individual 104 and the prosthesis 102 remain stationary and the individual's 104 attention is focused on the screen 128 and on generating distinct muscle contractions. During real-time use, both the individual 104 and the prosthesis 102 are actively moving, and the individual 104 is focused on the prosthesis 102 and the functional task at hand. However, under day-to-day, real-time conditions, the pattern of EMG signal generation for a distinct movement can change depending on positioning, current movement state, and whether the prosthesis 102 is carrying a load. During execution of the autoconfiguring pattern recognition training algorithm 300, EMG signal data can be captured while the prosthesis 102 is moving, which can produce more robust stored signal parameters 214 for use in classification 212. Further, the individual 104 consistency can be improved because the visual attention of the individual 104 can be focused on the prosthesis 102 during calibration and real-time use.

Finally, the repeated training sequence of the device prompting stage 304 can benefit the individual 104. As a result, the quality and repeatability of the elicited EMG signal data can be improved, as can the individual's 104 comfort level with the prosthesis guided training system 100. Also, by repeating the sequence and movements, a number of sessions required to produce satisfactory performance of the prosthesis guided training system 100 can be reduced.

EXAMPLES

The following section is intended as examples of the use of the prosthesis guided training system 100 according to some embodiments of the invention. The following examples are not to be construed as limitations.

For example, the individual's 104 enjoyment and comfort with the prosthesis guided training system 100 was assessed by sampling the preferences of five upper-extremity amputees as test subjects. Each of the subjects had undergone a targeted muscle reinnervation surgical procedure. Three of the subjects had a shoulder disarticulation prosthesis 102 and two of the subjects had a transhumeral prosthesis 102. Each of the subjects previously used a prosthesis 102 that included a real-time pattern recognition control algorithm 200. Moreover, each of the test subjects had experience with conventional screen guided prosthesis training systems that are similar to the above-noted conventional training system. Each of the test subjects participated in at least two clinical sessions where the test subjects trained and calibrated their prostheses 102 using the prosthesis guided training system 100, including execution of the autoconfiguring pattern recognition training algorithm 300. More specifically, each of the test subjects performed a repetitive functional task and was allowed to recalibrate their prosthesis 102 by executing the autoconfiguring pattern recognition training algorithm 300, at their convenience. In some sessions, EMG signal data received by EMG sensors 116 and disruptions were simulated in order to investigate the efficacy of recalibration when executing the autoconfiguring pattern recognition training algorithm 300. Following these sessions, test subjects provided feedback via a questionnaire, as shown in Tables 1 and 2 of respective FIGS. 6 and 7. Table 1 includes test subjects' responses to a questionnaire including Likert items, with 1 being a "Strongly Disagree" value and 5 being a "Strongly Agree" value. Table 2 includes test subjects' fill-in-the-blank responses to questions prompted by investigators.

As illustrated by the results shown in Table 1, the test subjects became comfortable with the prosthesis guided training system 100 and enjoyed executing the autoconfiguring pattern recognition training algorithm 300 to recalibrate and retrain their prostheses 102. More specifically, the test subjects stated that they would be more likely to use their prostheses 102 if they could train and calibrate it themselves at home. Moreover, the test subjects believed that the prosthesis guided training system 100 was easy to use and was not tiring. Additionally, the test subjects stated that by repeating the same sequence of self-actuations and motions during the device prompting stage 304, it was easier to complete the autoconfiguring pattern recognition training algorithm 300. As shown in Table 1, the test subjects also would have felt comfortable training or executing the autoconfiguring pattern recognition training algorithm 300 in front of others. Additionally, as shown in Table 2, the test subjects would be willing to regularly execute the autoconfiguring pattern recognition training algorithm 300 multiple times during a day of use to ensure adequate use of their prostheses 102.

Additionally, investigators carried out other experiments to directly compare the prosthesis 102 trained with the prosthesis guided training system 100 relative to the screen guided prosthesis training system. In this experiment, two subjects were used to assess the efficacy of the prosthesis guided training system 100 relative to the conventional system. The first subject has a shoulder disarticulation prosthesis 102 and the second subject had a transhumeral prosthesis 102.

In order to assess the efficacy of the prosthesis guided training system 100 relative to the conventional system, the test subjects trained and calibrated their respective prostheses 102 with both the prosthesis guided training system 100 and the screen guided prosthesis system. After each training and calibration, the test subjects were asked to perform a clothespin placement test to measure real-time controllability of their prostheses 102. The clothespin placement test includes moving clothespins from a horizontal bar to a vertical bar and requires the use of the elbow, wrist, and hand. The time required to move three clothespins was recorded and the test was repeated until the subjects completed three tests without dropping a clothespin.

The test subjects more quickly completed the clothespin placement test when they trained their prostheses 102 with the prosthesis guided training system 100 relative to the conventional system. More specifically, the first subject completed the clothespin placement test in average times of 50.5±10.3 seconds and 37.7±5.4 seconds with the screen guided prosthesis training system and the prosthesis guided training system 100, respectively. Similarly, the second subject completed the clothespin placement test in average times of 25.5±5.8 seconds and 21.8±2.6 seconds with the screen guided prosthesis training system and the prosthesis guided training system 100, respectively.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method for training a prosthesis comprising:
    calibrating a prosthesis, by:
        generating a sequence of automated movements of the prosthesis, the sequence of automated movements being predetermined and self-actuated by the prosthesis;
        instructing a user of the prosthesis to mimic each movement in the sequence of automated movements of the prosthesis;
        receiving, at a processor, electromyographic signal data generated in response to the user mimicking the sequence of automated movements of the prosthesis; and
        generating calibration classifier parameters, by:
            extracting, at the processor, at least one signal feature from the electromyographic signal data, and
            applying, using the processor, at least one machine learning algorithm to the at least one signal feature.

2. The method of claim 1, further comprising:
    determining, via the processor and based on the calibration classifier parameters derived from the electromyographic signal data, a motion intent for the prosthesis during real-time operation of the prosthesis,
    wherein determining the motion intent comprises identifying an output class defining a user intended movement for the prosthesis.

3. The method of claim 2, wherein determining the motion intent comprises identifying an estimated level of actuation for the prosthesis.

4. The method of claim 2, wherein determining the motion intent comprises identifying an estimated level of actuation for the prosthesis, and further comprising:
    processing the output class and the estimated level of actuation to generate a command signal to actuate the prosthesis.

5. The method of claim 1, further comprising:
    assessing a position of the prosthesis prior to starting the sequence of automated movements to determine whether the prosthesis is in a non-resting position; and
    returning the prosthesis to a rest position when the prosthesis is determined to be in the non-resting position.

6. The method of claim 1, wherein the at least one signal feature is at least one of a time-based signal feature, a frequency-based signal feature, and an auto-regressive model coefficient.

7. The method of claim 1, wherein the calibration classifier parameters comprise at least one of weight data, offset data, node data, model data, neuron data, and vector data.

8. The method of claim 1, wherein the processor is incorporated within the prosthesis and wherein the electromyographic signal data is received by at least one of a plurality of sensors in communication with the processor.

9. The method of claim 1, wherein generating the calibration classifier parameters further includes referencing additional electromyographic data generated where the user terminates mimicking the sequence of automated movements of the prosthesis, the additional electromyographic data defining a threshold level of electromyographic activity.

10. A system for training a prosthesis comprising:
a prosthesis;
a plurality of sensors associated with the prosthesis operable to detect electromyographic activity generated in response to a sequence of automated joint movements of the prosthesis, such electromyographic activity representing mimicking of the automated joint movements, and generate electromyographic signal data from the electromyographic activity;
a processor in communication with the prosthesis to:
receive the electromyographic signal data from the plurality of sensors; and
determine, based on the electromyographic signal data, a motion intent for the prosthesis during real-time operation of the prosthesis, by
generating calibration classifier parameters, by:
extracting, at the processor, at least one signal feature from the electromyographic signal data, and
applying, using the processor, at least one machine learning algorithm to the at least one signal feature.

11. The system of claim 10, wherein the motion intent comprises an output class defining one or more desired movements for the prosthesis.

12. The system of claim 11, wherein the motion intent further comprises an estimated level of actuation.

13. The system of claim 12, wherein the processor is configured to generate a command directing a movement of the prosthesis, wherein the command is based on the output class and the estimated level of actuation for the prosthesis.

14. The system of claim 10, wherein the signal feature is at least one of a time-based signal feature, a frequency-based signal feature, and an auto-regressive model coefficient.

15. The system of claim 10, wherein the calibration classification parameters comprise at least one of weight data, offset data, node data, model data, neuron data, and vector data.

16. The system of claim 11, wherein the processor is incorporated into the prosthesis.

17. The system of claim 11, wherein the prosthesis is trained in real-time.

18. The system of claim 11, wherein the processor is configured to:
determine a position of the prosthesis;
determine whether the position of the prosthesis is a non-resting position; and
generate one or more commands to return the prosthesis to a rest position when the prosthesis is determined to be in the non-resting position.

19. The system of claim 10, wherein the processor is in communication with the prosthesis to determine the motion intent for the prosthesis during real-time operation by:
extracting a portion of the electromyographic signal data based on the at least one signal feature;
defining at least one signal parameter based on the portion of electromyographic signal data; and
calculating an estimated level of actuation for the prosthesis based on the at least one signal parameter.

* * * * *